(12) United States Patent
Gormley et al.

(10) Patent No.: US 10,035,150 B2
(45) Date of Patent: Jul. 31, 2018

(54) SYSTEM FOR SUPPLYING ADDITIVE FLUIDS WITHIN A WASTE DISPOSAL WATER SUPPLY SYSTEM

(71) Applicant: General Electric Company, Schenectady, NY (US)

(72) Inventors: Joseph Emil Gormley, Louisville, KY (US); Jedediah Taylor Dawson, Crestwood, KY (US)

(73) Assignee: Haier US Appliance Solutions, Inc., Wilmington, DE (US)

( * ) Notice: Subject to any disclaimer, the term of this patent is extended or adjusted under 35 U.S.C. 154(b) by 906 days.

(21) Appl. No.: 14/532,070

(22) Filed: Nov. 4, 2014

(65) Prior Publication Data

US 2016/0122986 A1    May 5, 2016

(51) Int. Cl.
*B02C 18/00* (2006.01)
*E03C 1/266* (2006.01)
*A61L 11/00* (2006.01)
*B02C 23/18* (2006.01)

(52) U.S. Cl.
CPC .......... *B02C 18/0092* (2013.01); *A61L 11/00* (2013.01); *B02C 18/0084* (2013.01); *B02C 23/18* (2013.01); *E03C 1/2665* (2013.01)

(58) Field of Classification Search
CPC ................ B02C 18/0092; B02C 18/0084
USPC ........................................ 241/46.012, 46.013
See application file for complete search history.

(56) References Cited

U.S. PATENT DOCUMENTS

| | | | |
|---|---|---|---|
| 2,880,941 A | 4/1959 | Fox et al. | |
| 3,034,734 A * | 5/1962 | Guth | E03C 1/2665 137/49 |
| 5,577,573 A | 11/1996 | Haga et al. | |
| 5,676,319 A * | 10/1997 | Stiggins | E03C 1/2665 241/46.012 |
| 5,721,411 A | 2/1998 | Ervin | |
| 5,856,173 A * | 1/1999 | Riley | E03C 1/2665 222/321.7 |
| 6,131,587 A * | 10/2000 | Chardack | A47K 10/46 134/102.3 |
| 2003/0026918 A1 | 2/2003 | Itai et al. | |

* cited by examiner

*Primary Examiner* — Faye Francis
(74) *Attorney, Agent, or Firm* — Dority & Manning, P.A.

(57) ABSTRACT

In one aspect, a water supply system for a waste disposal may generally include a supply conduit configured to be fluidly connected to a water supply, wherein the supply conduit has a discharge end. The system may also include a disposal conduit in fluid communication with the supply conduit and a supplementary conduit in fluid communication with a storage tank containing an additive fluid. The supplementary conduit may be configured to supply the additive fluid into the flow of water directed through the disposal conduit to create a water/additive fluid mixture within the disposal conduit. Moreover, an outlet end of the disposal conduit may be configured to be in fluid communication with a disposal inlet of the waste disposal such that the water/additive fluid mixture directed through the disposal conduit is received within the waste disposal.

20 Claims, 8 Drawing Sheets

SYSTEM FOR SUPPLYING ADDITIVE FLUIDS WITHIN A WASTE DISPOSAL WATER SUPPLY SYSTEM

FIELD OF THE INVENTION

The present subject matter relates generally to waste disposals and, more particularly, to a system for supplying additive fluids into a flow of water directed into a waste disposal from a secondary water supply system.

BACKGROUND OF THE INVENTION

Waste disposal units are typically used to process solid waste, such as food waste, garbage and/or other waste, into particulates small enough to pass through associated drain plumbing. A conventional waste disposal is configured to be mounted onto a sink drain extending downward from a corresponding sink such that water/waste discharged from the sink may be directed into the disposal. The water/waste is typically directed into a grind chamber defined above a cutting or grinding mechanism of the disposal. The grinding mechanism is coupled to a shaft of a corresponding motor to allow the grinding mechanism to be rotated at high speeds. The waste contained within the grind chamber is typically ground, shredded, cut and/or otherwise processed into small particulates as a result of the rotation of the grinding mechanism relative to a stationary cutter ring extending around the outer perimeter of the grinding mechanism. The water and processed waste may then be discharged from the disposal and transmitted through the associated plumbing.

Typically, when a waste disposal is operating, water is supplied to the disposal via the faucet of the associated sink. Unfortunately, users often forget to turn on the water when operating the waste disposal, leading to dry operation (also referred to as dry running) of the disposal. Such dry operation increases the likelihood of damage occurring to one or more of the disposal components, thereby potentially reducing the operational life of the waste disposal. Moreover, even when the water is turned on during operation of a waste disposal, the amount of water received within the disposal may be insufficient to completely flush out the disposal. As a result, a significant amount of the processed waste may remain within the disposal after it is turned off. Such a build-up of processed waste within the disposal may often produce an undesirable odor and/or lead to performance issues.

Accordingly, a system for supplying water to a secondary inlet of a waste disposal for cleaning the disposal and/or for preventing dry operation of the disposal would be welcomed in the technology. Moreover, when supplying water to the secondary inlet of the waste disposal, it is desirable to allow an additive fluid to be mixed within the flow of water to provide for improved cleaning and/or enhanced operation of the waste disposal.

BRIEF DESCRIPTION OF THE INVENTION

Aspects and advantages of the invention will be set forth in part in the following description, or may be obvious from the description, or may be learned through practice of the invention.

In one aspect, the present subject matter is directed to a water supply system for a waste disposal. The water supply system may generally include a water supply conduit configured to be in fluid communication with a first water supply, wherein the water supply conduit has a water discharge end. The system may also include a disposal conduit in fluid communication with the water supply conduit. The disposal conduit may include an inlet end and an outlet end. The disposal conduit may also be spaced apart from the water supply conduit such that an air gap is defined between the inlet end and the water discharge end, wherein the inlet end is configured to receive water expelled from the water supply conduit via the water discharge end. In addition, the system may include a supplementary conduit configured to be in fluid communication with a storage tank containing an additive fluid. The supplementary conduit may be configured to supply the additive fluid into the flow of water directed through the disposal conduit to create a water/additive fluid mixture within the disposal conduit. In addition, the outlet end of the disposal conduit may be configured to be in fluid communication with a disposal inlet of the waste disposal such that the water/additive fluid mixture directed through the disposal conduit is received within the waste disposal.

In another aspect, the present subject matter is directed to a water supply system for a waste disposal. The water supply system may generally include a first supply conduit configured to be in fluid communication with a dishwasher and a second supply conduit configured to be in fluid communication with a separate water supply. The first supply conduit may include a first discharge end and the second supply conduit may include a second discharge end. The system may also include a disposal conduit in fluid communication with the first and second supply conduits. The disposal conduit may include an inlet end and an outlet end. The disposal conduit may also be spaced apart from the first and second conduits such that an air gap is defined between the inlet end and the first and second discharge ends, wherein the inlet end is configured to receive water expelled from the first and second supply conduits via the first and second discharge ends. In addition, the system may include a supplementary conduit configured to be in fluid communication with a storage tank containing an additive fluid. The supplementary conduit may be configured to supply the additive fluid into the flow of water directed through the disposal conduit to create a water/additive fluid mixture within the disposal conduit. Moreover, the outlet end of the disposal conduit may be configured to be in fluid communication with a disposal inlet of the waste disposal such that the water/additive fluid mixture directed through the disposal conduit is received within the waste disposal.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems and related methods for enhancing the operation and/or increasing the operational life of a waste disposal. Specifically, in several embodiments, the present subject matter is directed to a water supply system for directing a secondary supply of water into a waste disposal. For instance, as will be described below, the water supply system may include first and second supply conduits in fluid communication with a disposal conduit via a sink air gap, with the disposal conduit being connected, in turn, to a secondary inlet of the waste disposal. In such an embodiment, the first supply conduit may be connected to an outlet of an associated dishwasher to allow water (and, potentially, food waste) expelled from the dishwasher to flow through the first supply conduit and subsequently be directed into the disposal conduit (via the air gap) for supplying such water to the waste disposal. In addition, the second supply conduit may be in fluid communication with a separate water source (e.g., by being connected to a water source upstream of the dishwater) to allow a secondary supply of water to be directed through the second supply conduit and into the disposal conduit (via the air gap) for supplying a separate or secondary flow of water to the waste disposal. Moreover, a suitable valve may be provided in operative association with the second supply conduit for controlling the supply of water through such conduit.

As will be described below, by allowing for a separate or secondary flow of water to be provided to a waste disposal (i.e., beyond the flow of water provided during operation of the dishwasher), numerous operating advantages may be provided to the waste disposal. Specifically, the secondary flow of water may be provided to prevent dry operation of the disposal, thereby avoiding the potential damage that may otherwise occur to various components of the disposal during such operation. In addition, the secondary flow of water may serve as a means for cleaning or flushing out the waste disposal.

Moreover, in several embodiments, an additive fluid system may be utilized in connection with the water supply system to allow an additive fluid to be mixed into the water being directed into the waste disposal via the disposal conduit. For example, an additive fluid(s), such as a deodorant(s), odor-neutralizing agent(s), fragrance(s), disinfectant(s), decomposition agent(s) and/or the like, may be directed into the flow of water supplied through the disposal conduit via the first and/or second supply conduit. The resulting mixture may then flow through the disposal conduit may be directed into the secondary inlet of the waste disposal.

As will be described below, in several embodiments, the additive fluid may be directed into the flow of water supplied through the disposal conduit via a passively controlled valve. Specifically, in one embodiment, a portion of the disposal conduit may be configured similar to a venturi tube and may include a constrained section having a reduced cross-sectional area. In such an embodiment, the flow of water through the constrained section may create a negative or suction pressure that serves to open a valve associated with a secondary conduit in fluid communication with the disposal conduit, thereby allowing the additive fluid to flow through the secondary conduit and into the disposal conduit.

Additionally, the present subject matter is also directed to an electrical switch that may be utilized to control the supply of power to one or more of the components of the disclosed water supply system and/or the disclosed additive fluid system. In several embodiments, the switch may be coupled to, supported by and/or otherwise provided on an air gap housing associated with the above-described air gap. Such placement of the switch may allow a user of the disclosed system(s) to easily and efficiently turn on/off one or more of the various system components described herein. For example, in one embodiment, the switch may be electrically connected to both the waste disposal and the valve associated with the second supply conduit such that, upon actuation of the switch, both the disposal and the valve may be powered on simultaneously, thereby allowing the secondary supply of water to be directed into the waste disposal while it is being operated.

Figure 1:
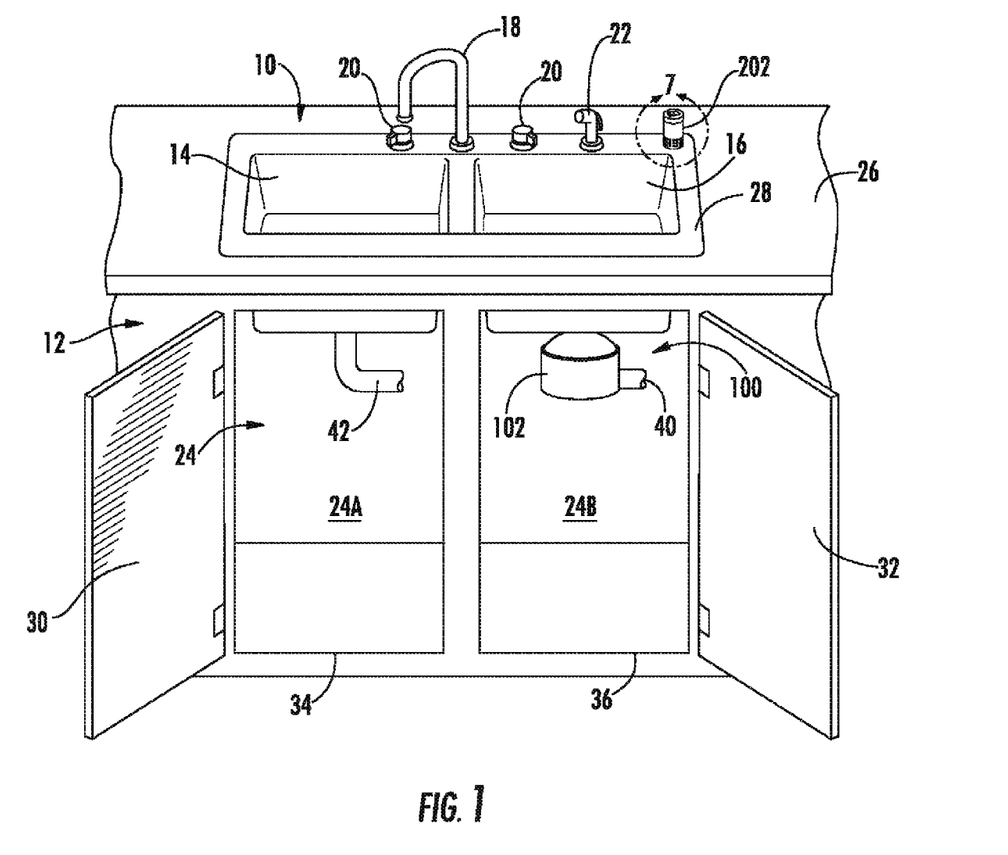
FIG. 1 illustrates a perspective view of a kitchen sink and associated under-sink cabinetry, particularly illustrating a waste disposal system installed within the under-sink cabinetry in accordance with aspects of the present subject matter.

Referring now to the drawings, FIG. 1 illustrates a perspective view of one embodiment of a kitchen sink 10 and associated under-sink cabinetry 12 in accordance with aspects of the present subject matter. As shown, the sink 10 is configured as a dual-bowl sink. Thus, the sink 10 includes a left or first sink bowl 14 and a right or second sink bowl 16 positioned side-by-side. However, in other embodiments, the sink 10 may have any other suitable configuration, such as by being configured as a single-bowl sink. As shown in FIG. 1, a faucet 18, knobs 20 and/or any other suitable accessories (e.g., a sink sprayer 22) may be associated with the sink 10. For example, as will be described in greater detail below, a sink air gap 202 may be associated with the sink 10.

In several embodiments, the sink 10 may be supported vertically above an under-sink storage space 24 via a countertop 26 and the associated cabinetry 12. Specifically, the sink 10 may include an outer rim 28 extending around its periphery that is configured to be engaged against the countertop 26 such that the sink bowls 14, 16 are received within a corresponding sink opening (not shown) defined in the countertop 26. The countertop 26 may, in turn, be positioned atop the cabinetry 12 such that cabinet doors 30, 32 associated with the cabinetry 12 may be utilized to access the under-sink storage space 24. For example, as shown in FIG. 1, a left or first cabinet door 30 may be mounted within a first opening 34 of the cabinetry 12 for providing direct access to a left or first portion 24A of the under-sink storage space 24. Additionally, a right or second cabinet door 32 may be mounted within a second opening 36 of the cabinetry 12 for providing direct access to a right or second portion 24B of the under-sink storage space 24. In such embodiment, each cabinet door 30, 32 may be selectively opened and closed to access and close-off, respectively, the under-sink storage space 24. In other embodiments, the cabinetry 12 may have any other suitable number of cabinet doors for accessing the under-sink storage space 24, such as a single cabinet door or three or more cabinet doors.

Additionally, as shown in FIG. 1, a waste disposal system 100 may be installed within the under-sink cabinetry 12. Specifically, the system 100 may include a waste disposal 102 positioned within the under-sink storage space 24. As shown in the illustrated embodiment, the waste disposal 102 is mounted in fluid communication with the second sink bowl 16. As such, water and/or waste discharged from the second sink bowl 16 may be processed by the waste disposal 102 and subsequently discharged therefrom via a suitable discharge pipe 40. In such an embodiment, a standard drain pipe 42 may be mounted to the first sink bowl 14 for draining water (and, potentially, waste) from the first sink bowl 14. Alternatively, the waste disposal 102 may be mounted in fluid communication with the first sink bowl 14, with the drain pipe 42 being mounted to the second sink bowl 16. As is generally understood, the discharge pipe 40 and the drain pipe 42 may be coupled to a common wastewater pipe (not shown) of the associated residential or building plumbing.

Figure 2:
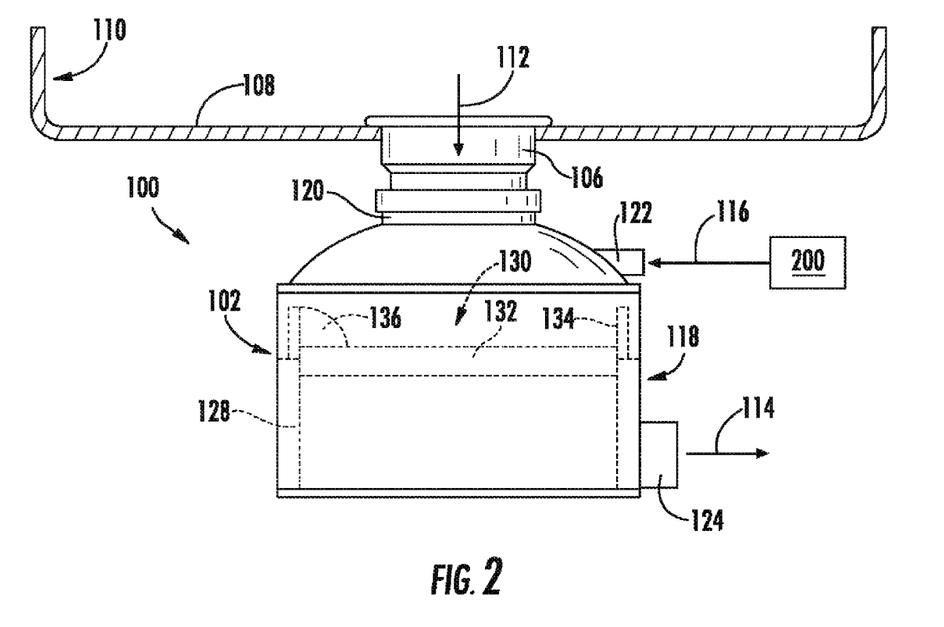
FIG. 2 illustrates a side view of the waste disposal system shown in FIG. 1.

Referring now to FIG. 2, a side view of one embodiment of the waste disposal system 100 described above is illustrated in accordance with aspects of the present subject matter. As shown, the system 100 may generally include a waste disposal 102 configured to be mounted to a sink drain 106 extending from the bottom of a sink bowl 108 of a corresponding sink 110 (e.g., the second sink bowl 16 of the sink 10 shown in FIG. 1). As is generally understood, while the sink 110 is being used, water and waste (e.g., food waste and other solid waste) may collect within the sink bowl 108 and may be subsequently discharged therefrom via the drain 106. The water and waste flowing through the drain 106 may then be directed into the waste disposal 102 (as indicated by arrow 112), wherein the waste may be processed into fine particulates. The water and processed waste may then be discharged from the waste disposal 102 (as indicated by arrow 114) into a suitable flow conduit or discharge line of the associated plumbing (e.g., the discharge pipe 40 shown in FIG. 1). Additionally, as shown in FIG. 2, the waste disposal 102 may also be configured to receive water and/or waste from a secondary water/waste source in fluid communication with the disposal 102 (as indicated by arrow 116). For example, in several embodiments, the flow 116 of water and/or waste may derive from a water supply system 200 fluidly connected to the waste disposal 102. Specifically, as will be described in greater detail below, the water supply system 200 may be configured to allow waste/water expelled from an associated dishwasher and/or water from a separate water source to be supplied to the waste disposal 102.

In general, the waste disposal 102 may include a housing 118 configured to form an outer casing or enclosure for the various other components of the disposal 102. In general, the housing 118 may have any suitable configuration that allows it to function as a casing or enclosure for the disposal components. For instance, the housing 118 may be formed from two or more housing components configured to be coupled to one another so as to form a complete housing assembly, such as by forming the housing from a upper housing portion configured to be coupled to a lower housing portion.

In addition, the housing 118 may define one or more inlets and outlets for receiving and discharging water and/or waste. For instance, a primary inlet 120 may be defined in the housing 118 (e.g., at the top of the housing 118) for receiving water/waste discharged from the sink 110 and a secondary inlet 122 may be defined in the housing 118 for receiving water and/or waste directed through the water supply system 200. In addition, a discharge outlet 124 may be defined in the housing 118 (e.g., at and/or adjacent to the bottom of the housing 118) for discharging water and processed waste from the disposal 102.

As shown in hidden lines in FIG. 2, the disposal 102 may also include a motor 128 and a cutter system 130 disposed within the housing 118. As is generally understood, the motor 128 may be configured to rotate a cutter plate 132 of the cutter system 130 directly below a grind chamber (not shown) defined within the housing 118 between the cutter plate 132 and the primary inlet 120. Thus, as the cutter plate 132 is rotated, water/waste entering the grind chamber via the primary inlet 120 may be directed radially outwardly along the plate 132 towards a stationary cutter ring 134 of the cutter system 130 disposed around the inner perimeter of the housing 118 (i.e., around the outer perimeter of the grind chamber). In addition, the cutter plate 132 may include a cutter lug 136 coupled thereto and/or extending therefrom for pushing waste flowing along the outer perimeter of the plate 132 into the adjacent cutter ring 134. The cutter ring 134 may, in turn, define a plurality of cutter slots (not shown) that serve to grind, shred, cut and/or otherwise process the waste. Accordingly, the waste flowing along the outer perimeter of the cutter plate 132 may be pushed by the cutter lug 136 into and/or against the cutter slots of the stationary cutter ring 134 in order to process the waste into fine particulates. The processed waste may then be discharged from the disposal 102 via the discharge outlet 124.

It should be appreciated that the motor 128 and the cutter plate 132 of the disclosed disposal 102 may generally have any suitable configuration known in the art that allows such components to function as described herein. For instance, in one embodiment, the motor 128 may have an outrunner or external rotor configuration. As such, the motor 128 may include a stator (not shown) and an external rotor (not shown) extending around the outer circumference of the stator. In such an embodiment, the cutter plate 132 may be formed integrally with the external rotor, such as by forming the cutter plate 132 as all or a portion of the top wall of the rotor, or the cutter plate 132 may be coupled to the rotor using any other suitable means, such as by using mechanical fasteners. In other embodiments, the motor 128 may have an internal rotor configuration and may include a shaft (not shown) extending outwardly therefrom. In such embodiments, the cuter plate 132 may be coupled to the motor shaft for rotation therewith.

It should also be appreciated that, in alternative embodiments, the waste disposal 102 may have any other suitable configuration known in the art that allows for the processing of water and/or waste flowing from a sink, dishwasher and/or any other waste/water source.

Figure 3:
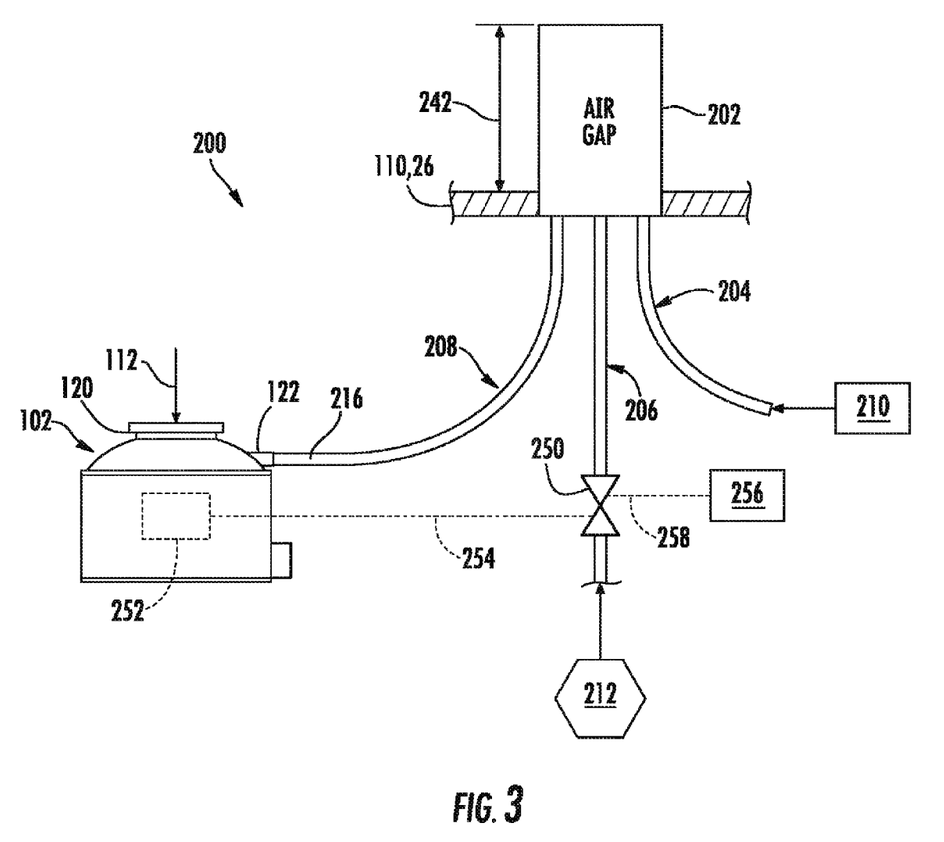
FIG. 3 illustrates a simplified view of one embodiment of a secondary water supply system that may be used in connection with a waste disposal system in accordance with aspects of the present subject matter.
Figure 4:
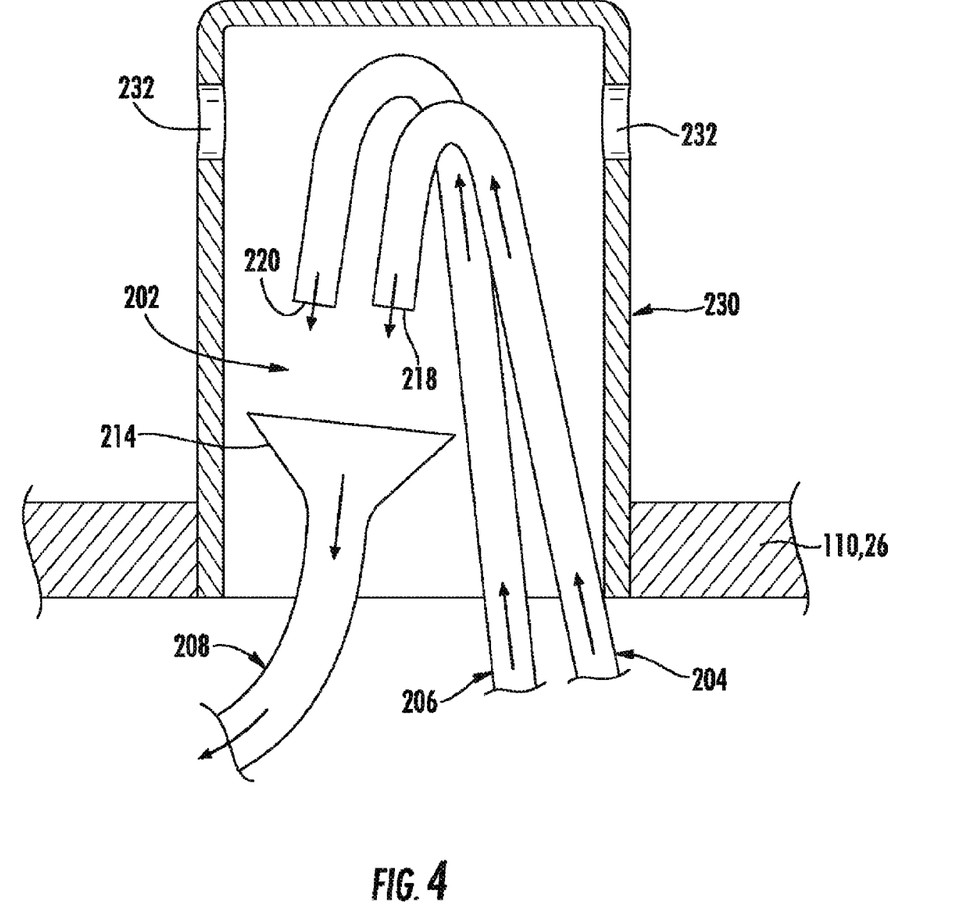
FIG. 4 illustrates a partial, cross-sectional view of one embodiment of an air gap configuration that may be utilized in accordance with aspects of the present subject matter.

Referring now to FIGS. 3 and 4, simplified views of one embodiment of a water supply system 200 that may be used in connection with a waste disposal system 100 is illustrated in accordance with aspects of the present subject matter. Specifically, FIG. 3 illustrates a schematic view of the water supply system 200 and FIG. 4 illustrates a cross-sectional view of an example configuration of an air gap 202 that may be formed between adjacent conduits 204, 206, 208 of the system 200.

As indicated above, during operation of a waste disposal 102, water is typically supplied into the disposal 102 from the sink 110 via its primary inlet 120 (e.g., as indicated by arrow 112 in FIG. 3). However, in accordance with aspects of the present subject matter, the disclosed system 200 may be configured to provide a secondary supply of water to the waste disposal 102 via the disposal's secondary inlet 122, thereby allowing water to be directed into the disposal 102 so as to prevent dry operation and/or to allow improved cleaning of the disposal 102.

As shown, the system 200 may include a first supply conduit 204 and a second supply conduit 206, with the first supply conduit 204 configured to be in fluid communication with an associated dishwasher 210 and the second supply conduit 206 configured to be in fluid communication with a separate water supply 212. Specifically, the first fluid conduit 204 may be connected directly or indirectly with an outlet (not shown) of the dishwasher 210 such that water, such as grey water, (and, potentially, food waste) expelled from the dishwasher 210 may be directed through the first supply conduit 204. Similarly, the second supply conduit 206 may be connected directly or indirectly to any suitable conduit or pipe through which water is directed without being first directed through the dishwasher 210. For example, the second supply conduit 206 may be connected directly or indirectly to the same upstream water supply pipe that provides water to the dishwasher 210 and/or to the sink 110 (FIG. 2) associated with the disposal 102 such that a supply of freshwater may be directed through the second supply conduit 206.

Each supply conduit 204, 206 may be configured to direct water from its respective water source to a disposal conduit 208 connected to the secondary inlet 122 of the waste disposal 102. Specifically, the disposal conduit 208 may include an inlet end 214 (FIG. 4) in fluid communication with both the first and second supply conduits 204, 206 and an outlet end 216 in fluid communication with the secondary inlet 122. As such, water directed through each supply conduit 204, 206 may flow through the disposal conduit 208 and into the waste disposal 102.

In several embodiments, each supply conduit 204, 206 may be configured to be in fluid communication with the disposal conduit 208 via an air gap 208 defined between adjacent ends of the conduits 204, 206, 208. Specifically, as shown in FIG. 4, the first supply conduit 206 may include a first discharge end 218 and the second supply conduit 206 may include a second discharge end 220, with each discharge end 218, 220 being spaced apart from the inlet end 214 of the disposal conduit 208 such that an air gap 202 is defined between the conduits 204, 206, 208. In such an embodiment, waster expelled from the discharge end 218, 220 of each supply conduit 204, 206 may flow through the air gap 202 into the inlet end 214 of the disposal conduit 208. Such water may then be directed through the disposal conduit 208 and into the garbage disposal 102 via its secondary inlet 122.

It should be appreciated that the air gap 202 formed between the adjacent conduits 204, 206, 208 may generally have any suitable configuration known in the art that provides an unobstructed vertical space between the discharge ends 218, 220 of the supply conduits 204, 206 and the inlet end 214 of the disposal conduit 208. For example, as shown in the illustrated embodiment, the supply conduits 204, 206 are curled downward adjacent to their discharge ends 218, 220 such that the ends 218, 220 are oriented towards the inlet end 214 of the disposal conduit 208, thereby allowing the water discharged from each supply conduit 204, 206 to flow directly through the air gap 202 and into the disposal conduit 208. In such an embodiment, as shown in FIG. 4, the inlet end 214 of the disposal conduit 208 may be enlarged (e.g., such as by defining an outwardly tapered profile) to ensure that the water discharged from each supply conduit 218, 220 is received within the disposal conduit 208. However, in an alternative embodiment, one or both of the discharge ends 218, 220 may have any other suitable orientation relative to the inlet end 214 of the disposal conduit 208 that permits water expelled from the supply conduits 204, 206 to flow through the air gap 202 and into the disposal conduit 208.

Additionally, in several embodiments, the air gap 202 may be defined within a corresponding housing 230 configured to receive portions of the supply conduits 204, 206 and/or the disposal conduit 208. For example, as shown in FIG. 4, portions of the supply conduits 204, 206 may be configured to extend upwardly within the housing 230 to a location at or adjacent to the top of the housing 230. Additionally, a portion of the disposal conduit 208 may be configured to extend into the housing 230 such that the inlet end 214 of the conduit 208 is positioned within the housing 230 at a location vertically below the discharge ends 218, 220 of the supply conduits 204, 206.

Figure 7:
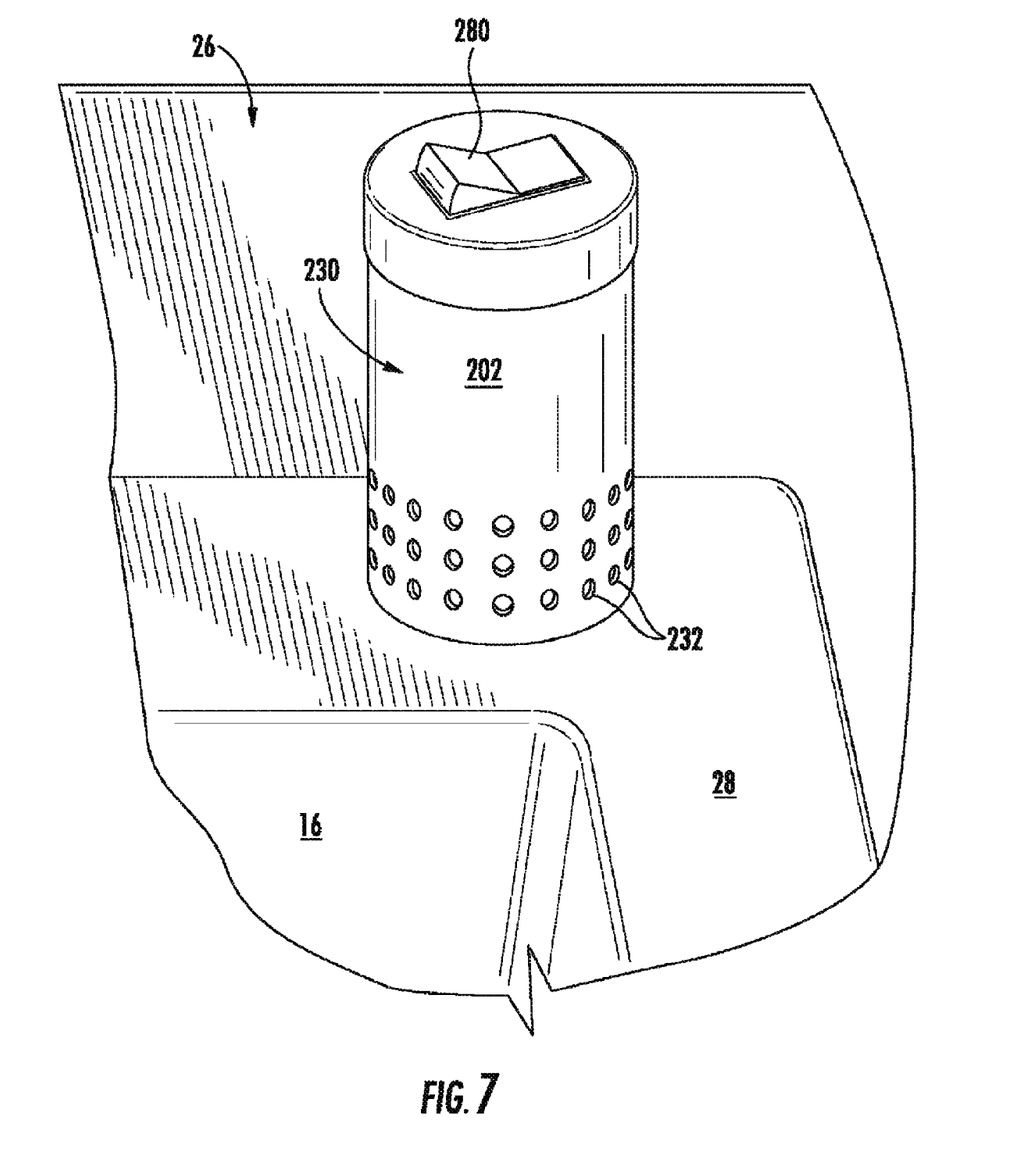
FIG. 7 illustrates a close-up, perspective view of a portion of the sink shown in FIG. 1, particularly illustrating one embodiment of an electrical switch that may be provided on the housing associated with the sink air gap.

It should be appreciated that the housing 230 may generally have any suitable configuration that allows it to function as described herein. For example, in several embodiments, the housing 230 may be cylindrically shaped (e.g., as shown in FIG. 7). However, in other embodiments, the housing 230 may define any other suitable shape. Additionally, as shown in FIG. 4, the housing 230 may define one or more air vents 232 to allow air to flow into and through the housing 230.

It should also be appreciated that the housing 230 may be configured to be positioned at any suitable vertical location that allows the air gap 202 to prevent back-flow into the dishwasher 210. For example, as shown in the illustrated embodiment, the housing 230 may be mounted to and/or supported by a portion of the sink 110 (e.g., along the outer rim 28 of the sink 10 shown in FIG. 1) and/or a portion of the countertop 26 (FIG. 1) such that the housing 230 extends above the sink/countertop 110/26 by a given vertical distance 242. Alternatively, the housing 230 may be configured to extend through the sink/countertop 110, 26 such that the housing 230 extends to locations both above and below the sink/countertop 110, 26. In a further embodiment, the housing 230 may be positioned entirely below the sink/countertop 110, 26.

Referring particularly to FIG. 3, in several embodiments, the system 200 may include a water valve 250 provided in operative association with the second supply conduit 206. In general, the water valve 250 may be configured to control the supply of water directed through the second supply conduit 206. For example, in one embodiment, the water valve 250 may correspond to a simple on/off valve. In such an embodiment, when in the OFF or closed position, the valve 250 may be configured to cut-off the supply of water through the second supply conduit 206 whereas, when in the ON or open position, the valve 250 may be configured to allow water to be directed from the water supply 212 through the second supply conduit 206 and into the disposal conduit 208 via the air gap 202. Alternatively, the water valve 250 may correspond to any other suitable valve known in the art. For example, the valve 250 may correspond to a pressure regulating valve (e.g., a solenoid activated, proportional valve) that allows the pressure of the water supplied through the second supply conduit 206 to be specifically controlled.

In general, the water valve 250 may be configured to be normally closed such that the supply of water through the second supply conduit 206 is turned off. However, when a given trigger event occurs, the valve 250 may be opened to allow water to be supplied through the second supply conduit 206 and subsequently directed into the waste disposal 102 via the disposal conduit 208. For example, in several embodiments, the water valve 250 may be configured to be opened when the waste disposal 102 is turned on and subsequently closed when the waste disposal 102 is no longer operating. In doing so, the valve 250 may be immediately closed when the waste disposal 102 is turned off or a delay period may be implemented such that water may continue to be supplied to the waste disposal 102 for a short period of time following the disposal 102 being turned off.

It should be appreciated that any suitable electrical arrangement and/or control configuration may be provided to allow the water valve 102 to be opened and closed based on the operation of the waste disposal 102. For instance, as shown in FIG. 3, in one embodiment, an internal controller 252 of the waste disposal 102 may be communicatively coupled to the water valve 250 (e.g., via connection 254). In such an embodiment, the internal controller 252 may be configured to transmit suitable control signals to the water valve 250 for opening the valve 250 when the waste disposal 102 is being operated and for subsequently closing the valve 250 when the waste disposal 102 is turned off. Alternatively, the water valve 250 may be communicatively coupled to a separate controller 256 external to the disposal 102 (e.g., via connection 258) that is configured to transmit suitable control signals for opening and closing the valve 250. For example, the controller 256 may be configured to detect when the disposal 102 is turned on/off and subsequently transmit control signals to the valve 250 for controlling its operation.

In other embodiments, the waste disposal 102 and the valve 250 may be connected via any suitable electrical arrangement that allows such components to be simultaneously powered on/off. Specifically, in one embodiment, the waste disposal 102 and the valve 250 may be electrically connected to a power source via a common switch or series of switches, thereby allowing the supply of power to both components to be controlled via actuation of the switch(es). For example, as will be described below with reference to FIGS. 7 and 8, both the waste disposal 102 and the valve 250 may be electrically connected to a common switch associated with the air gap housing 230. In such an embodiment, the switch may allow the waste disposal 102 and the valve 250 to be powered on/off simultaneously, thereby allowing water to be directed through the second supply conduit 206 and into the waste disposal 102 via the disposal conduit 208 while the disposal 102 is being operated.

By configuring the water valve 250 to open when the waste disposal 102 is turned on, dry operation of the disposal 102 may be completely prevented. Specifically, conventional waste disposal systems rely on the user turning on the associated faucet 18 (FIG. 1) to allow water to be directed into the disposal 102 via its primary inlet 120. Unfortunately, users often forget to turn on the water, thereby leading to dry operation of the disposal 102. However, using the disclosed system 200, the waste disposal 102 may be supplied with water while it is being operated regardless of whether any water is being received within the disposal 102 via its primary inlet 120.

It should be appreciated that, as an alternative to simply activating the water valve 250 when the disposal 102 is turned on, the valve 250 may be opened and/or closed based any other suitable trigger event. For example, when the operation of the valve 250 is being controlled via a suitable controller (e.g., the internal controller 252 or the separate controller 256), the controller 252, 256 may be configured to actively control the operation of the valve 250 based on one or more sensed operating conditions of the disposal 102 and/or based on any other suitable operating parameter(s). For instance, in one embodiment, the controller 252, 256 may be configured to detect when the waste disposal 102 is being operated dry (e.g., via a suitable sensor provided within the disposal 102) and subsequently open the valve 240 to allow water to be supplied to the disposal 102 via its secondary inlet 122. In such an embodiment, the disclosed system 200 may provide increased efficiency by maintaining the valve 250 in its closed position when it is determined that water is being supplied to the waste disposal 102 via the sink 110.

In another embodiment, the controller 252, 256 may be configured to implement an automatic cleaning mode in which water is supplied to the waste disposal 102 in order to flush out or otherwise clean the disposal 102. For example, the controller 252, 256 may be communicatively coupled to a suitable sensor configured to provide an indication that the waste disposal 102 needs to be flushed out (e.g., an odor sensor or a sensor that detects waste build-up within the disposal 102). In such an embodiment, the controller 252, 256 may be configured to open the valve 250 to allow water to be directed into the disposal for cleaning purposes. Alternatively, the controller 252, 256 may include an internal clock or timing mechanism that allows the controller 252, 256 to monitor the time interval(s) between each use and/or each cleaning of the disposal 102. In such instance, the controller 252, 256 may, for example, be configured to periodically open the valve 250 (e.g., once a week) to provide a cleansing flow of water through the disposal 102.

It should be appreciated that, as used herein, the term "controller" generally refers to any suitable computing device and/or processing unit known in the art. As such, each controller described herein may, for example, include one or more processor(s) and associated memory device(s) configured to perform a variety of computer-implemented functions (e.g., performing the functions described herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) included within a given controller may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) may generally be configured to store suitable computer-readable instructions that, when implemented by the processor(s), configure the associated controller to perform various functions.

Figure 5:
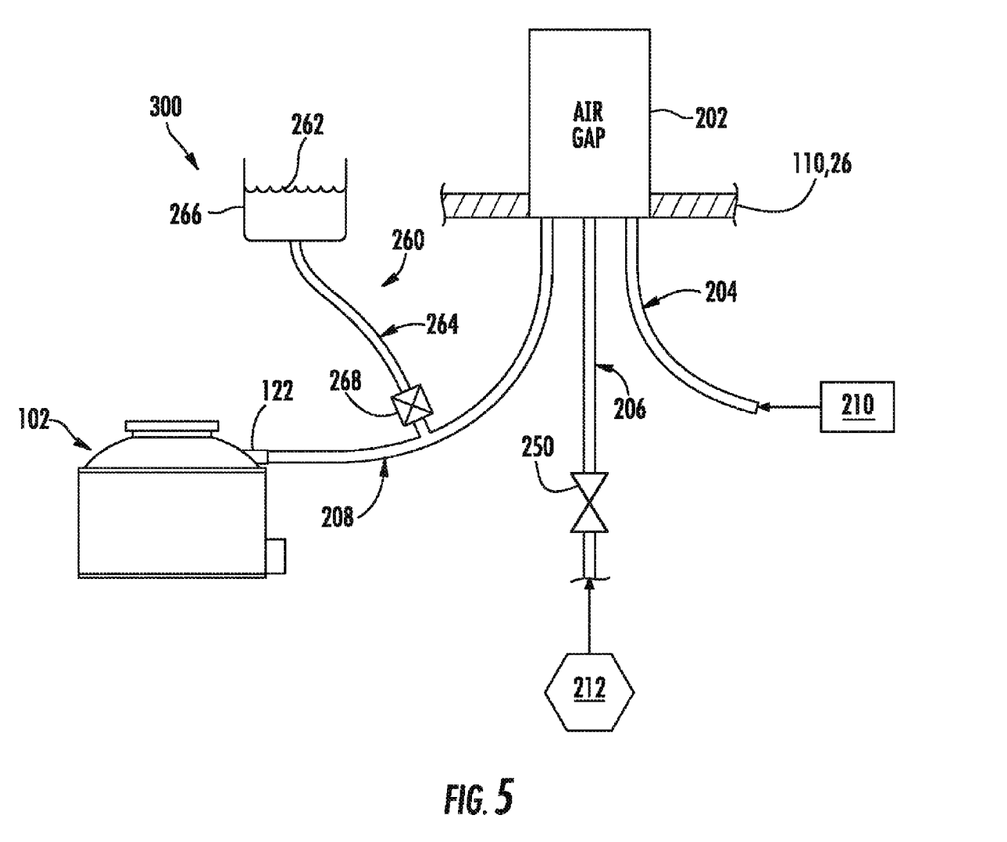
FIG. 5 illustrates a simplified view of another embodiment of a secondary water supply system that may be used in connection with a waste disposal system in accordance with aspects of the present subject matter, particularly illustrating one embodiment of an additive fluid system that allows an additive fluid to be directed into the flow of water supplied through the secondary water supply system.
Figure 6:
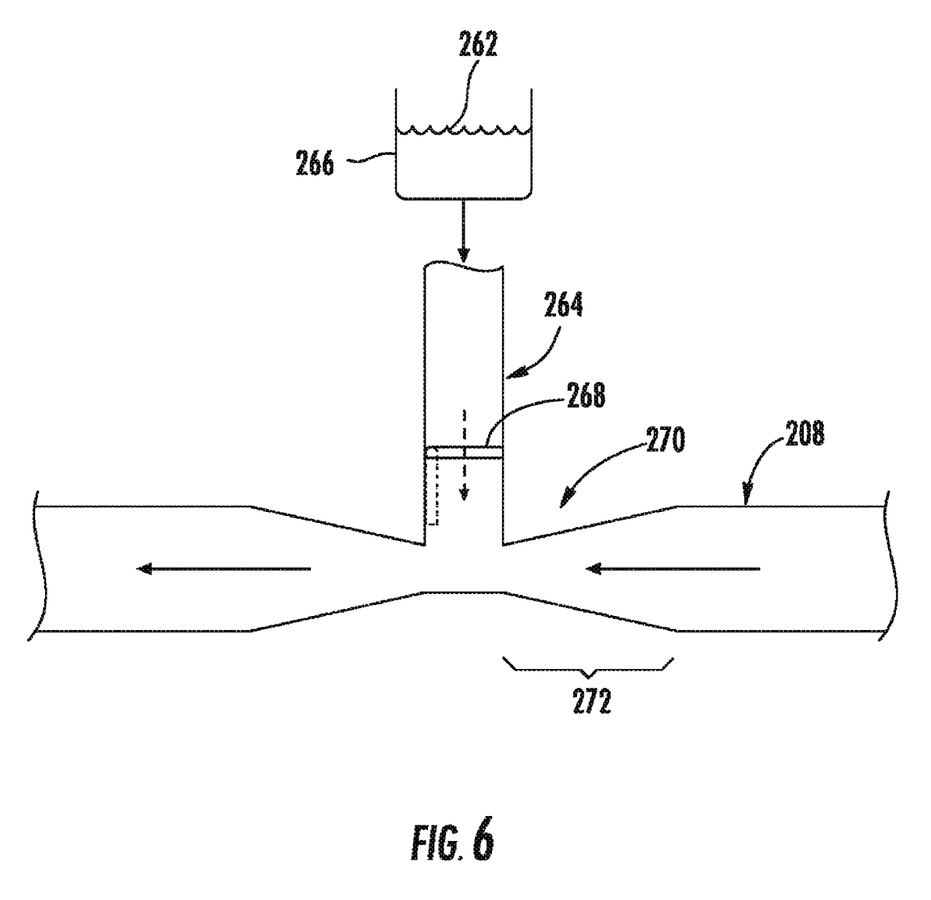
FIG. 6 illustrates a simplified view of one embodiment of a suitable configuration for passively controlling a valve associated with the additive fluid system shown in FIG. 5.

Referring now to FIGS. 5 and 6, another embodiment of a water supply system 300 that may be used in connection with a waste disposal system 100 is illustrated in accordance with aspects of the present subject matter. As shown in FIG. 5, the system 300 may include many or all of the same system components described above with reference to FIGS. 3 and 4. For instance, the system 300 may include first and second supply conduits 204, 206 in fluid communication with a disposal conduit 208 via an air gap 202. Similar to that described above, the first supply conduit 204 may be in fluid communication with an associated dishwasher 210 while the second supply conduit 206 may be in fluid communication with a separate water supply 212, with both conduits terminating at respective discharge ends (not shown) at the air gap 202. In addition, the disposal conduit 208 may be configured to receive water expelled from the supply conduits 204, 206 and direct such water into the waste disposal 102 via its secondary inlet 122. Moreover, as shown in FIG. 5, a water valve 250 may also be provided for controlling the supply of water directed through the second supply conduit 206 and into the waste disposal 102 via the disposal conduit 208. As indicated above, the valve 250 may be configured to be turned on/off based on any suitable trigger event, such as when the waste disposal 102 is turned on/off, when the disposal 102 is running dry, when the disposal 102 needs to be cleaned or flushed out and/or based on any other suitable trigger event.

Additionally, as shown in FIG. 5, the system 300 may also include a secondary system 260 for supplying an additive fluid 261 into the flow of water being directed through the disposal conduit 208 and into the waste disposal 102. Specifically, in several embodiments, the disposal conduit 208 may be in fluid communication with a supplementary conduit 264 configured to receive an additive fluid 262 from a given fluid source 266 (e.g., a fluid tank or other vessel). In such embodiments, as water is flowing through the disposal conduit 208, the additive fluid 262 may be directed into the flow of water such that the resulting water/additive fluid mixture may be supplied into the waste disposal 102.

It should be appreciated that, in general, the additive fluid 262 may correspond to any suitable fluid(s) desired to be supplied into the waste disposal 102. For example, in one embodiment, the additive fluid 262 may be deodorizer or other suitable agent or solution for neutralizing odors within the disposal 102. In another embodiment, the additive fluid 262 may correspond to a fragrance or other suitable scented fluid selected to provide a desired scent for the disposal 102. In a further embodiment, the additive fluid 262 may correspond to a disinfectant or other suitable cleaning agent/solution configured to kill bacteria or otherwise provide for improved cleaning of the disposal 102. In yet another embodiment, the additive fluid 262 may correspond to a solution including a decomposition agent for assisting in slowing, halting or speeding up of the decomposition of organic compounds contained within the disposal 102 and/or within any other downstream component(s) (e.g., the septic system). Of course, the additive fluid 262 may also correspond to any suitable combination of agents, solutions, chemicals, enzymes and/or the like. For example, in one embodiment, the additive fluid 262 may correspond to a combination of a disinfectant together with an odor neutralizer or fragrance.

As shown in the FIG. 5, the flow of additive fluid 262 into the disposal conduit 208 may, in several embodiments, be controlled via an additive valve 268 provided in operative association with the supplementary conduit 264. In general, the additive valve 268 may correspond to any suitable valve that allows for the flow of additive fluid 262 into the disposal conduit 208 to be passively or actively controlled. For instance, FIG. 6 illustrates one embodiment of a suitable configuration that allows the additive valve 268 to be passively controlled based on the flow of water through the disposal conduit 208.

As shown in FIG. 6, in one embodiment, a portion of the disposal conduit 208 extending adjacent to the intersection between the disposal conduit 208 and the supplementary conduit 264 may be configured similar to a venturi tube and, thus, may include a constrained section 270 defining a reduced cross-sectional area. In such an embodiment, as water is directed into the disposal conduit 208 and flows through the constrained section 270, a venturi effect may occur as the velocity of the water increases with decreases in the cross-sectional area (e.g., across a coned or tapered section 272 of the conduit 208), thereby creating a negative or suction pressure within the adjacent supplementary conduit 264. The suction pressure generated within the supplementary conduit 264 may result in the corresponding additive valve 268 being opened, thereby allowing additive fluid 262 to be supplied into the flow of water directed through the disposal conduit 208. For example, as shown in FIG. 6, in one embodiment, the additive valve 268 may correspond to a suction valve or any other suitable valve (e.g., a flap valve, etc.) that is configured to be actuated to an opened position (e.g., indicated by the dashed lines) when a negative pressure is generated within the supplementary conduit 264 due to the flow of water through the constrained section 270 of the disposal conduit 208. Thereafter, once the pressure returns to normal, the valve 268 may return to a closed position to prevent the additive fluid 262 from flowing through the supplementary conduit 264 and into the disposal conduit 208.

Alternatively, the operation of the additive valve 268 may be configured to be actively controlled. For instance, in several embodiments, the additive valve 268 may correspond to an electronically controlled valve configured to be opened and closed in response to suitable control signals transmitted to the valve 268 via a suitable controller (e.g., the internal controller 252 or the separate controller 256 described above). In such embodiments, the additive valve 258 may, for example, be configured to be opened when water is flowing through the disposal conduit 208 and subsequently closed thereafter. For example, the additive valve 258 may be communicatively coupled to the same electronic controller 252, 256 and/or electrically coupled to the same circuit as the water valve 250 such that both valves 250, 268 are opened and closed simultaneously.

Referring now to FIG. 7, a perspective view of a portion of the sink 10 shown in FIG. 1 is illustrated in accordance with aspects of the present subject matter, particularly illustrating one embodiment of an air gap switch 280 that may be utilized in connection with the disclosed system(s) 200, 300. Specifically, in several embodiments, an electrical switch 180 may be coupled to, supported by or otherwise associated with the air gap housing 230 for selectively powering any and/or all of the various system components described above. As indicated above, the air gap housing 230 may be mounted to or otherwise supported by a portion of the sink 10 and/or an adjacent portion of the countertop 26 such that the housing 230 extends vertically upwardly therefrom. In such an embodiment, the air gap switch 280 may be conveniently positioned on or within the housing 230 at any suitable location that permits a user to access the switch when standing near the sink 10 (e.g., at a location at or adjacent to the top of the housing 230).

As shown in the illustrated embodiment, the air gap switch 280 corresponds to a mechanical switch that is configured to be manually toggled between ON/OFF positions for controlling the supply of power to one or more of the system component(s). However, in other embodiments, the air gap switch 280 may correspond to any other suitable switching mechanism or device known in the art, such as a capacitive touch switch, a Hall Effect switch, a Reed switch and/or the like. Similarly, the signal communications for the switch 280 may be accomplished using any suitable means, such as by using a wire(s) and an associated slip ring(s). Alternatively, the wire/slip ring may be replaced with any other suitable signal communications means, such as an optical connection, an inductive connection and/or a wireless connection (e.g., using WiFi, Bluetooth, or Near Field Communications (NFC) protocols).

Figure 8:
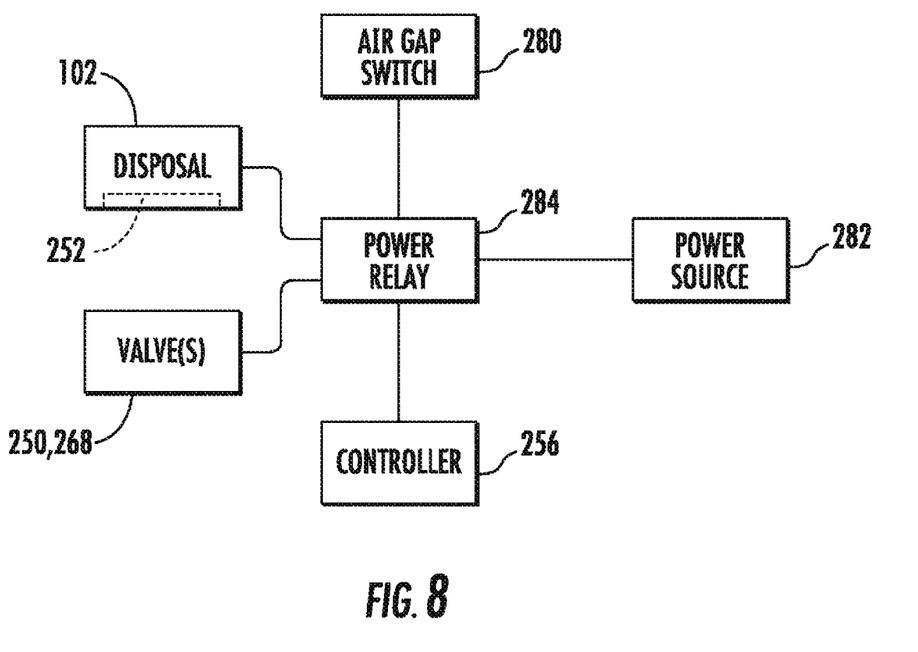
FIG. 8 illustrates a schematic view of one embodiment of an electrical arrangement for controlling the power supplied to one or more system components via the air gap switch shown in FIG. 7.

Referring now to FIG. 8, one embodiment of a suitable electrical arrangement that may be utilized to control the power supply to one or more of the various system components described above with reference to FIGS. 3-6 using the disclosed air gap switch 280 is illustrated in accordance with aspects of the present subject matter. As shown, the air gap switch 280 may be utilized to control the supply of power from a suitable power source 282 (e.g., the utility grid) to one or more of the system component(s) via a power relay 284. In such embodiments, the air gap switch 280 may be connected to the power relay 284 such that, when the switch is actuated, the power relay 284 is opened/closed so to control the supply of power to the system component(s). For example, actuation of the air gap switch 280 to an "ON" position may result in the power relay 284 being closed, thereby allowing power to be supplied to the system component(s). Similarly, actuation of the air gap switch 280 to an "OFF" position may result in the power relay 284 being opened, thereby cutting off the supply of power to the system component(s).

In alternative embodiments, any other suitable electrical arrangement may be provided to allow the air gap switch 280 to directly or indirectly control the supply of power to the system component(s). For example, as an alternative to the power relay 284, any other suitable switching mechanism(s) and/or device(s) may be provided to electrically couple the various system components to the power source 282. Similarly, in another embodiment, the air gap switch 280 may be directly coupled between the system component(s) and the power source 282 for controlling the supply of power to such components(s).

In several embodiments, any number of the various components described above with reference to FIGS. 3-6 may be configured to be powered on/off via actuation of the air gap switch 280. For example, as shown in FIG. 8, the waste disposal 102 (including, optionally, the internal controller 252), the controller 252 and the valve(s) (e.g., the water valve 250 and/or the additive valve 268) may be electrically connected to the air gap switch 280 via the power relay 284. However, in other embodiments, only one of the above described components or any other combination of such components may be configured to be powered on/off via actuation of the air gap switch 280. For instance, in one embodiment, the air gap switch 280 may only be configured to control the supply of power to the waste disposal 102, thereby allowing the disposal 102 to be turned on/off. Alternatively, the air gap switch 280 may only be electrically connected to the waste disposal 102 and the water valve 250, thereby allowing such components to be powered simultaneously via actuation of the air gap switch 280.

It should be appreciated that, in addition to controlling the power supplied to one or more of the various system components (or as an alternative thereto), the air gap switch 280 may be configured to control the supply of power to any other suitable electrical components. For instance, the power supplied to various other electrical components located within the proximity of the sink 10, such as one or more lights, fans and/or the like, may be controlled via actuation of the air gap switch 280.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A water supply system comprising:
   a waste disposal;
   a water supply conduit configured to be in fluid communication with a first water supply, the water supply conduit having a water discharge end;
   a disposal conduit in fluid communication with the water supply conduit, the disposal conduit including an inlet end and an outlet end, the disposal conduit being spaced apart from the water supply conduit such that an air gap is defined between the inlet end and the water discharge end, the inlet end being configured to receive water expelled from the water supply conduit via the water discharge end; and
   a supplementary conduit configured to be in fluid communication with a storage tank containing an additive fluid, the supplementary conduit being configured to supply the additive fluid into the flow of water directed through the disposal conduit at an intersection of the disposal conduit and the supplementary conduit located between the inlet and outlet ends of the disposal conduit to create a water/additive fluid mixture within the disposal conduit,
   wherein the outlet end of the disposal conduit is configured to be in fluid communication with a disposal inlet of the waste disposal such that the water/additive fluid mixture directed through the disposal conduit is received within the waste disposal.

2. The water supply system of claim 1, wherein the additive fluid comprises at least one of a deodorizer, a fragrance, a disinfectant or a decomposition agent.

3. The water supply system of claim 1, wherein an additive valve is provided in operative association with the supplementary conduit, the additive valve being configured to control the flow of additive fluid from the storage tank through the supplementary conduit.

4. The water supply system of claim 3, wherein the additive valve is configured to be actively or passively controlled.

5. The water supply system of claim 3, wherein the disposal conduit includes a constrained section defining a reduced cross-sectional area at a location adjacent to the intersection between the disposal conduit and the supplementary conduit.

6. The water supply system of claim 5, wherein, when water is directed through the constrained section, a negative pressure is generated within the supplementary conduit that actuates the additive valve to an opened position such that the additive fluid is directed into the flow of water through the disposal conduit and mixed therewith to create the water/additive fluid mixture.

7. The water supply system of claim 1, further comprising a water valve provided in operative association with the water supply conduit, the water valve being configured to control the flow of water from the first water supply through the water supply conduit.

8. The water supply system of claim 7, wherein the valve is configured to be actuated to an opened position when the waste disposal is being operated to allow water to flow through the water supply conduit and into the disposal conduit.

9. The water supply system of claim 1, further comprising a dishwasher conduit in fluid communication with a dishwasher, the dishwasher conduit having a dishwasher discharge end terminating at the air gap such that water expelled from the dishwasher is directed into the dishwasher conduit and then flows across the air gap and into the disposal conduit.

10. The water supply system of claim 1, wherein the first water supply corresponds to a water supply separate from the dishwasher.

11. The water supply system of claim 1, wherein the disposal inlet corresponds to a secondary inlet of the waste disposal, the waste disposal further comprising a. primary inlet separate from the secondary inlet that is configured to receive water from an associated sink.

12. A water supply system comprising:
a waste disposal;
a first supply conduit configured to be in fluid communication with a dishwasher, the first supply conduit having a first discharge end;
a second supply conduit configured to be in fluid communication with a separate water supply, the second supply conduit having a second discharge end;
a disposal conduit in fluid communication with the first and second supply conduits, the disposal conduit including an inlet end and an outlet end, the disposal conduit being spaced apart from the first and second conduits such that an air gap is defined between the inlet end and the first and second discharge ends, the inlet end being configured to receive water expelled from the first and second supply conduits via the first and second discharge ends; and
a supplementary conduit configured to be in fluid communication with a storage tank containing an additive fluid, the supplementary conduit being configured to supply the additive fluid into the flow of water directed through the disposal conduit to create a water/additive fluid mixture within the disposal conduit,
wherein the outlet end of the disposal conduit is configured to be in fluid communication with a disposal inlet of the waste disposal such that the water/additive fluid mixture directed through the disposal conduit is received within the waste disposal.

13. The water supply system of claim 12, wherein the additive fluid comprises at least one of a deodorizer, a fragrance, a disinfectant or a decomposition agent.

14. The water supply system of claim 12, wherein an additive valve is provided in operative association with the supplementary conduit, the additive valve being configured to control the flow of additive fluid from the storage tank through the supplementary conduit.

15. The water supply system of claim 14, wherein the additive valve is configured to be actively or passively controlled.

16. The water supply system of claim 14, wherein the disposal conduit includes a constrained section defining a reduced cross-sectional area at a location adjacent to an intersection between the disposal conduit and the supplementary conduit.

17. The water supply system of claim 16, wherein, when water is directed through the constrained section, a negative pressure is generated within the supplementary conduit that actuates the additive valve to an opened position such that the additive fluid is directed into the flow of water through the disposal conduit and mixed therewith to create the water/additive fluid mixture.

18. The water supply system of claim 12, further comprising a water valve provided in operative association with the second supply conduit, the water valve being configured to control the flow of water from the second water supply through the second supply conduit.

19. The water supply system of claim 18, wherein the valve is configured to be actuated to an opened position when the waste disposal is being operated to allow water to flow through the water supply conduit and into the disposal conduit.

20. A water supply system comprising:
a waste disposal;
a water supply conduit configured to be in fluid communication with a first water supply, the water supply conduit having a water discharge end;
a disposal conduit in fluid communication with the water supply conduit, the disposal conduit including an inlet end and an outlet end, the disposal conduit being spaced apart from the water supply conduit such that an air gap is defined between the inlet end and the water discharge end, the inlet end being configured to receive water expelled from the water supply conduit via the water discharge end; and
a supplementary conduit configured to be in fluid communication with a storage tank containing an additive fluid, the supplementary conduit being configured to supply the additive fluid into the flow of water directed through the disposal conduit to create a water/additive fluid mixture within the disposal conduit,
wherein the outlet end of the disposal conduit is configured to be in fluid communication with a disposal inlet of the waste disposal such that the water/additive fluid mixture directed through the disposal conduit is received within the waste disposal,
wherein the additive fluid is introduced to the flow of water directed through the disposal conduit at a location downstream of the air gap.

* * * * *